US011375978B2

(12) United States Patent
 Irie (10) Patent No.: US 11,375,978 B2
(45) Date of Patent: Jul. 5, 2022

(54) ULTRASOUND ENDOSCOPE

(71) Applicant: OLYMPUS CORPORATION, Tokyo (JP)

(72) Inventor: Kei Irie, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 861 days.

(21) Appl. No.: 16/184,097

(22) Filed: Nov. 8, 2018

(65) Prior Publication Data

US 2019/0069878 A1 Mar. 7, 2019

Related U.S. Application Data

(63) Continuation of application No. PCT/JP2017/011187, filed on Mar. 21, 2017.

(30) Foreign Application Priority Data

May 18, 2016 (JP) .............................. JP2016-099318

(51) Int. Cl.
 *A61B 8/00* (2006.01)
 *A61B 8/12* (2006.01)
 (Continued)

(52) U.S. Cl.
 CPC .............. *A61B 8/445* (2013.01); *A61B 1/008* (2013.01); *A61B 1/0057* (2013.01); *A61B 8/12* (2013.01); *A61B 8/4466* (2013.01); *A61B 8/4494* (2013.01)

(58) Field of Classification Search
 None
 See application file for complete search history.

(56) References Cited

U.S. PATENT DOCUMENTS 5,271,382 A * 12/1993 Chikama .............. A61B 1/0055
 138/120
2010/0036258 A1* 2/2010 Dietz ................... G10K 11/355
 600/466
(Continued)

FOREIGN PATENT DOCUMENTS

JP H11-305143 A 11/1999
JP 2004-016725 A 1/2004
(Continued)

OTHER PUBLICATIONS

Helix. https://mathworld.wolfram.com/Helix.html. 2021 (Year: 2021).*
(Continued)

*Primary Examiner* — Luther Behringer
(74) *Attorney, Agent, or Firm* — Scully, Scott, Murphy & Presser, P.C.

(57) ABSTRACT

An ultrasound endoscope includes: a transducer unit arranged on a distal end side in an insertion direction to an inside of a subject and configured to transmit and receive an ultrasonic wave; a bendable tube arranged on a proximal end side relative to the transducer unit, the bendable tube including a plurality of ring-shaped members that are joined with each other along the insertion direction and bendable in at least two directions; a flexible tube arranged to be continuous to the proximal end side of the bendable tube; and a flexible board inserted to an inside of the bendable tube and configured to electrically connect the transducer unit. The flexible board includes a helical portion that is formed in a helical shape following an inner surface of the bendable tube, and that is fixed to the inner surface of the bendable tube at a part.

16 Claims, 5 Drawing Sheets

(51) Int. Cl.
  *A61B 1/005* (2006.01)
  *A61B 1/008* (2006.01)

(56) References Cited

U.S. PATENT DOCUMENTS

| | | | |
|---|---|---|---|
| 2011/0166455 A1* | 7/2011 | Cully | A61B 8/4466 |
| | | | 600/463 |
| 2013/0303919 A1 | 11/2013 | Corl | |
| 2015/0164469 A1 | 6/2015 | Corl | |
| 2015/0305598 A1* | 10/2015 | Yamashita | A61B 1/0055 |
| | | | 604/95.04 |

FOREIGN PATENT DOCUMENTS

| | | |
|---|---|---|
| JP | 2010-005148 A | 1/2010 |
| WO | WO 2013/170150 A1 | 11/2013 |

OTHER PUBLICATIONS

International Search Report dated Jun. 13, 2017 issued in PCT/JP2017/011187.

* cited by examiner

ULTRASOUND ENDOSCOPE

CROSS REFERENCES TO RELATED APPLICATIONS

This application is a continuation of PCT International Application No. PCT/JP2017/011187 filed on Mar. 21, 2017 which claims the benefit of priority from Japanese Patent Application No. 2016-099318, filed on May 18, 2016, the entire contents of which are incorporated herein by reference.

BACKGROUND

The present disclosure relates to an ultrasound endoscope.

Ultrasound endoscopes to observe an internal body of a subject, such as a human, by inserting a flexible elongated insertion portion into a body of the subject have been known. Such an ultrasound endoscope includes a transducer unit that transmits and receives ultrasonic waves, a bendable tube that is arranged on a proximal end side relative to the transducer unit and that may be bent according to an operation input to an operating unit, a flexible tube that is provided in a continuous manner to a proximal end side of the bendable tube, and a signal cable that is inserted through the bendable tube and the flexible tube, and that is electrically connected to the transducer unit.

However, in this structure, the signal cable is bent according to a bending movement of the bendable tube and, therefore, the signal cable may be deteriorated.

Therefore, as a structure to prevent the deterioration of the signal cable, a following ultrasound endoscope has been proposed (for example, refer to Japanese Laid-open Patent Publication No. 2004-16725).

In the ultrasound endoscope described in Japanese Laid-open Patent Publication No. 2004-16725, a signal cable is not routed to the inside of a bendable tube (bendable portion), but a structure in which a flexible board is arranged inside the bendable tube, and electrical connection with a signal cable that is routed to a transducer unit (ultrasound probe) and a distal end side of the bendable tube is achieved with this flexible board is applied. Moreover, the flexible board is arranged inside the bendable tube, helically wound about an axis of the bendable tube, leaving a small gap from the bendable tube. Inside the helical structure of the flexible board, a content, such as a treatment-tool insertion channel to put through a treatment tool, is inserted along an axis of the helical structure.

The flexible board may be pulled toward a proximal end side with an operation input to the operating unit. In the ultrasound endoscope described in Japanese Laid-open Patent Publication No. 2004-16725, when the flexible board is pulled toward the proximal end side as described above, the content inside the helical structure of the flexible board is to be squeezed by the flexible board. If such an action (action of squeezing a content with the flexible board) is repeated, the flexible board may be broken, and the content may be damaged.

SUMMARY

An ultrasound endoscope according to one aspect of the present disclosure includes: a transducer unit arranged on a distal end side in an insertion direction to an inside of a subject, the transducer unit being configured to transmit and receive an ultrasonic wave; a bendable tube arranged on a proximal end side relative to the transducer unit, the bendable tube including a plurality of ring-shaped members that are joined with each other along the insertion direction and bendable in at least two directions; a flexible tube arranged to be continuous to the proximal end side of the bendable tube; and a flexible board inserted to an inside of the bendable tube, the flexible board being configured to electrically connect the transducer unit, wherein the flexible board includes a helical portion that is formed in a helical shape following an inner surface of the bendable tube, and that is fixed to the inner surface of the bendable tube at a part.

The above and other features, advantages and technical and industrial significance of this disclosure will be better understood by reading the following detailed description of presently preferred embodiments of the disclosure, when considered in connection with the accompanying drawings.

DETAILED DESCRIPTION

An embodiment is explained below, referring to the drawings. The embodiment explained below is not intended to limit the present disclosure. Furthermore, like reference symbols are assigned to like components throughout the drawings.

Schematic Configuration of Endoscope System

Figure 1:
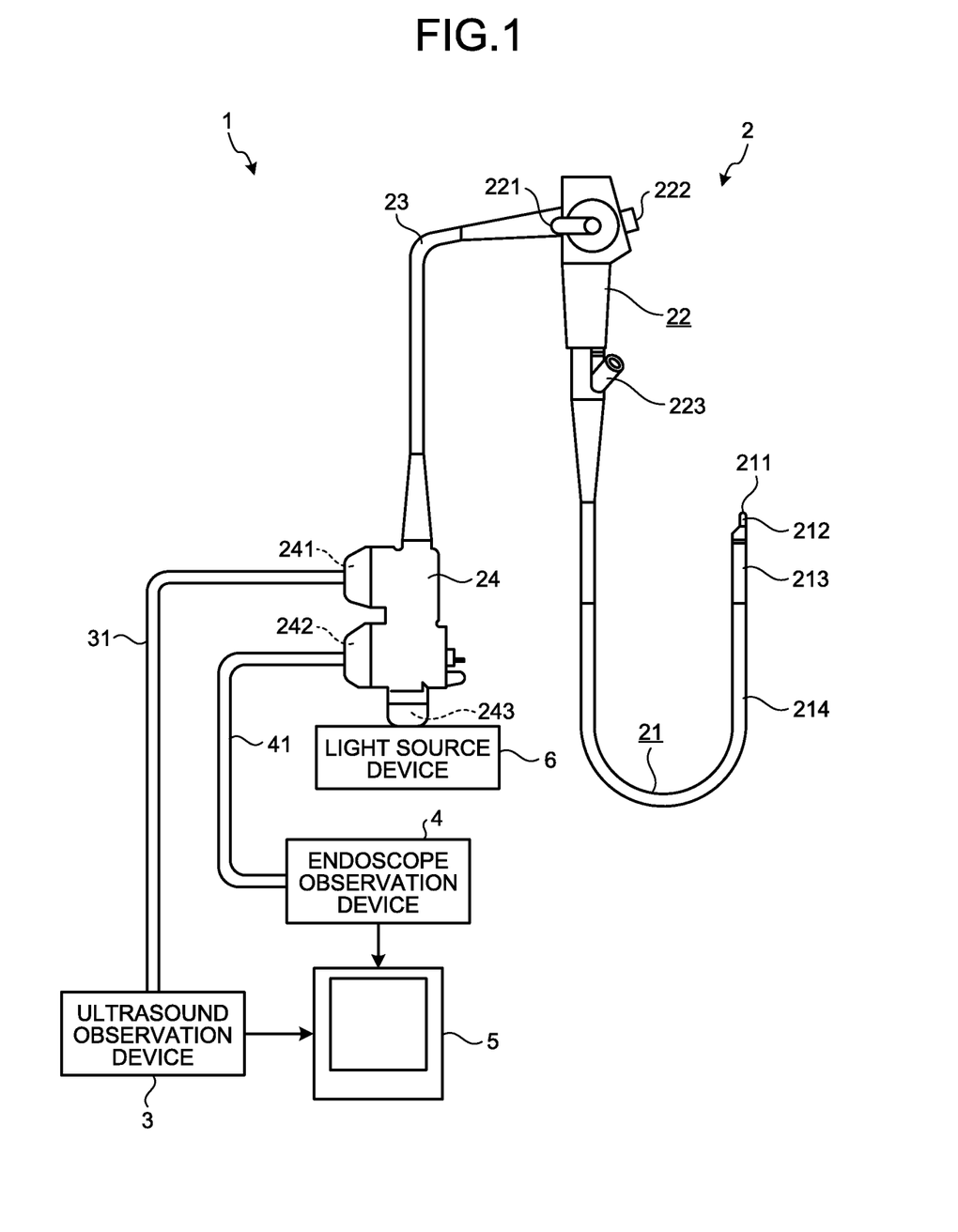
FIG. 1 is a schematic diagram of an endoscope system according to an embodiment.

FIG. 1 is a schematic diagram of an endoscope system 1 according to an embodiment.

The endoscope system 1 is a system to perform ultrasonic diagnosis inside a subject, such as a human, by using an ultrasound endoscope. This endoscope system 1 includes, as illustrated in FIG. 1, an ultrasound endoscope 2, an ultrasound observation device 3, an endoscope observation device 4, a display device 5, and a light source device 6.

The ultrasound endoscope 2 can be inserted into a subject at a part, and has a function of transmitting ultrasonic pulses toward a body wall, and of receiving ultrasound echoes reflected by the subject to output an echo signal, and a function of outputting an image signal by imaging the inside of the subject.

A detailed configuration of the ultrasound endoscope 2 is described later.

The ultrasound observation device 3 is electrically connected to the ultrasound endoscope 2 through an ultrasonic cable 31 (FIG. 1), and outputs a pulse signal to the ultrasound endoscope 2 and receives an echo signal from the ultrasound endoscope 2 through the ultrasonic cable 31. The ultrasound observation device 3 subjects the echo signal to predetermined processing to generate an ultrasound image.

The endoscope observation device 4 is electrically connected to the ultrasound endoscope 2 through a video cable 41 (FIG. 1), and receives an image signal from the ultrasound endoscope 2 through the video cable 41. The endoscope observation device 4 subjects the image signal to predetermined processing to generate an endoscopic image.

The display device 5 is constituted of a liquid crystal or organic electroluminescence (EL), and displays the ultrasound image generated by the ultrasound observation device 3, or the endoscopic image generated by the endoscope observation device 4.

The light source device 6 is connected to the ultrasound endoscope 2 through a connector 24 (third connector unit 243) provided in the ultrasound endoscope 2, described later, and supplies illumination light to illuminate the inside of the subject to the ultrasound endoscope 2.

Configuration of Ultrasound Endoscope

The ultrasound endoscope 2 includes an insertion portion 21, an operating unit 22, a universal cable 23, and a connector 24 as illustrated in FIG. 1.

A term "distal end side" used in the following means a side closer to a distal end of the insertion portion 21 (a distal end side in an insertion direction into a body of a subject). Moreover, a term "proximal end side" used in the following means a side away from the distal end of the insertion portion 21.

The insertion portion 21 is a portion to be inserted into the body of the subject. This insertion portion 21 includes an ultrasound probe 211 that is arranged on the distal end side, a rigid member 212 that is connected to a proximal side of the ultrasound probe 211, a bendable portion 213 that is connected to a proximal end side of the rigid member 212 and that can be bent, and a flexible tube 214 that is connected to a proximal end side of the bendable portion 213 as illustrated in FIG. 1.

Inside the insertion portion 21, a light guide LG (refer to FIG. 5) that transmits illumination light supplied from the light source device 6, an image guide IG (refer to FIG. 5) that transmits a subject image toward the proximal end side, a tube TB (refer to FIG. 5) that is used to send air, water, and the like, a treatment tool tube CH (refer to FIG. 5) to insert through a treatment tool (for example, puncture needle or the like), a signal cable CB (refer to FIG. 2) to transmit the pulse signal or the echo signal described above, a flexible board FPC (refer to FIG. 5) that electrically connects a transducer unit 2111 (refer to FIG. 2), described later, constituting the ultrasound probe 211 and the signal cable CB, and the like are routed.

A detailed configuration (the ultrasound probe 211, the rigid member 212, the bendable portion 213, and the flexible board FPC) on the distal end side of the insertion portion 21 is described later.

The operating unit 22 is a portion that is connected to the proximal end side of the insertion portion 21, and that accepts various kinds of operations from a doctor, or the like. This operating unit 22 includes a bending knob 221 to bend the bendable portion 213, and plural operating members 222 to perform various kinds of operations as illustrated in FIG. 1.

Furthermore, in the operating unit 22, a treatment-tool insertion inlet 223 that communicates with the treatment tool tube CH provided inside the insertion portion 21 to insert a treatment tool into the treatment tool tube CH therefrom is formed.

Moreover, inside the operating unit 22, an imaging device (not illustrated) that images a subject image transmitted through the image guide IG and outputs an image signal, and an optical system (not illustrated) that forms an image of the subject image transmitted through the image guide IG on the imaging device are provided.

The universal cable 23 is a cable that extends from the operating unit 22, and in which plural signal cables (not illustrated) to transmit various signals, an optical fiber (not illustrated) to transmit illumination light supplied from the light source device 6, and the like are arranged.

The connector 24 is arranged at an end portion of the universal cable 23. The connector 24 includes first to third connector portions 241 to 243 to which the ultrasonic cable 31, the video cable 41, and the light source device 6 are connected, respectively.

Configuration of Insertion Portion

Figure 2:
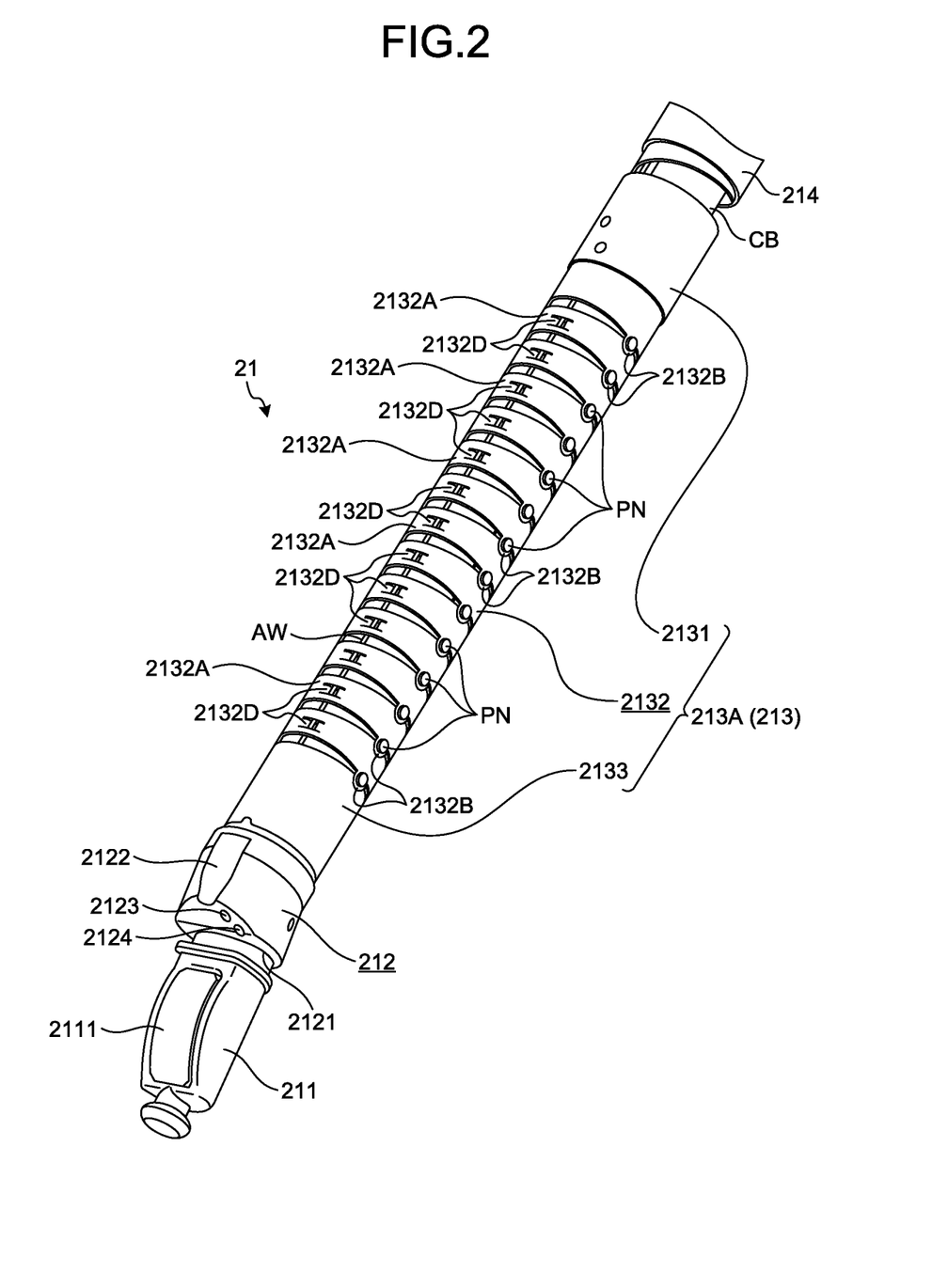
FIG. 2 is an enlarged perspective view of a distal end side of an insertion portion illustrated in FIG. 1.

FIG. 2 is an enlarged perspective view of the distal end side of the insertion portion 21.

Configurations of the ultrasound probe 211, the rigid member 212, the bendable portion 213, and the flexible board FPC are sequentially explained below.

Configuration of Ultrasound Probe

The ultrasound probe 211 is a convex ultrasound probe, and has the transducer unit 2111 in which multiple ultrasound transducers are regularly arranged to form a convex arc shape as illustrated in FIG. 2.

The ultrasound transducer has an acoustic lens, a piezoelectric device, and a matching layer, and acquires an ultrasonic echo contributing to obtain an ultrasound tomography image deeper inside of a body wall inside the subject.

The transducer unit 2111 converts a pulse signal received from the ultrasound observation device 3 through the flexible board FPC and the signal cable CB routed inside the insertion portion 21 into an ultrasonic pulse to transmit to the inside of the subject. Furthermore, the transducer unit 2111 converts an ultrasonic echo reflected inside the subject into an electrical echo signal to output to the ultrasound observation device 3 through the flexible board FPC and the signal cable CB routed inside the insertion portion 21.

Configuration of Rigid Member

In the rigid member 212, a mounting hole 2121, a treatment tool channel 2122, an imaging hole 2123, and an illumination hole 2124 are formed as illustrated in FIG. 2.

The mounting hole 2121 is a hole in which the ultrasound probe 211 is mounted.

The treatment tool channel 2122 is a hole from which various kinds of treatment tools that are inserted through the treatment tool tube CH from the treatment-tool insertion inlet 223 protrudes out.

The imaging hole 2123 is a hole in which one end of the image guide IG is arranged, and that takes in a subject image into the end the image guide IG.

The illumination hole 2124 is a hole in which one end of the light guide LG is arranged, to illuminate the inside of the subject with the illumination light transmitted through the light guide LG.

Configuration of Bendable Portion

The bendable portion 213 includes a bendable tube 213A having a proximal end base 2131, plural ring-shaped members 2132, and a distal end base 2133, a shield member 2134 (refer to FIG. 5), and a covering member 2135 (refer to FIG. 5) as illustrated in FIG. 2. In FIG. 2, illustration of the shield member 2134 and the covering member 2135 is omitted (only the bendable tube 213A is illustrated) for convenience of explanation.

The proximal end base 2131 has a cylindrical shape, and is connected to the flexible tube 214 on its proximal end side.

The distal end base 2133 has a cylindrical shape, and is connected to the rigid member 212 on its distal end side.

Figure 5:
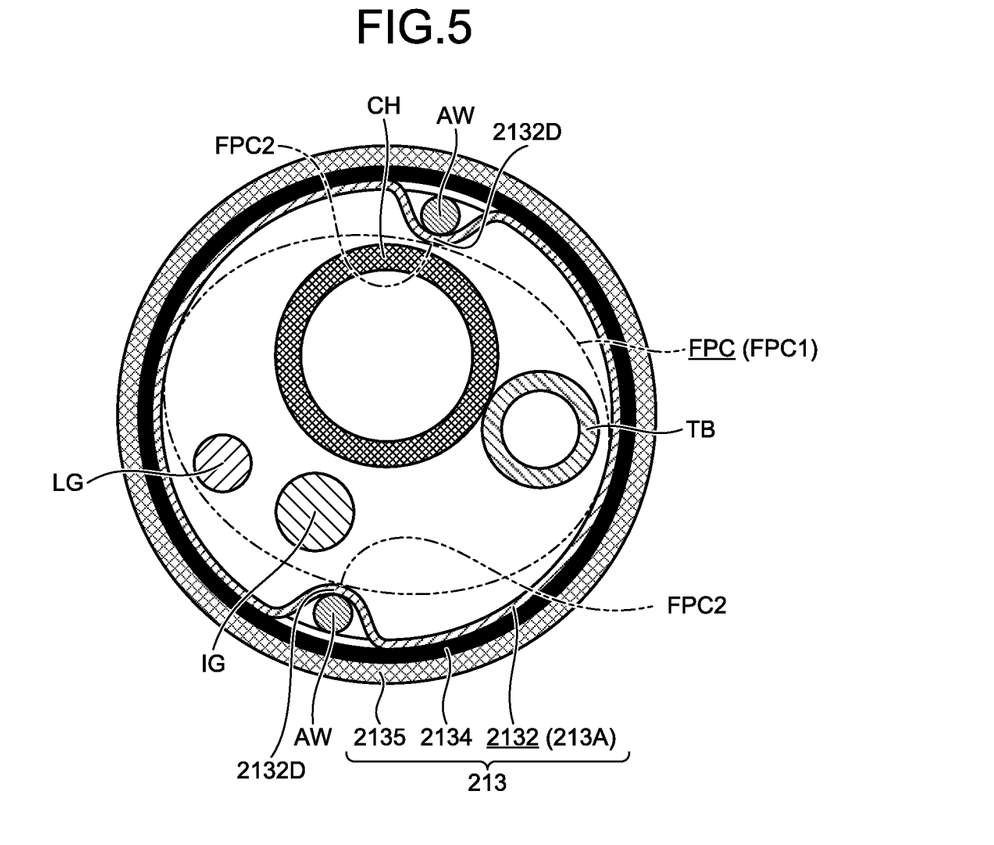
FIG. 5 shows arrangement of the flexible board arranged inside the bendable portion illustrated in FIG. 1 and FIG. 2.

The shield member 2134 is a shield member of a metal mesh or the like provided for electromagnetic compatibility (EMC) or noise suppression purpose, and is a member that covers an outer periphery of the bendable tube 213A.

The covering member 2135 is structured with a flexible material, such as rubber, and is a member that covers an outer periphery of the shield member 2134.

Figure 3:
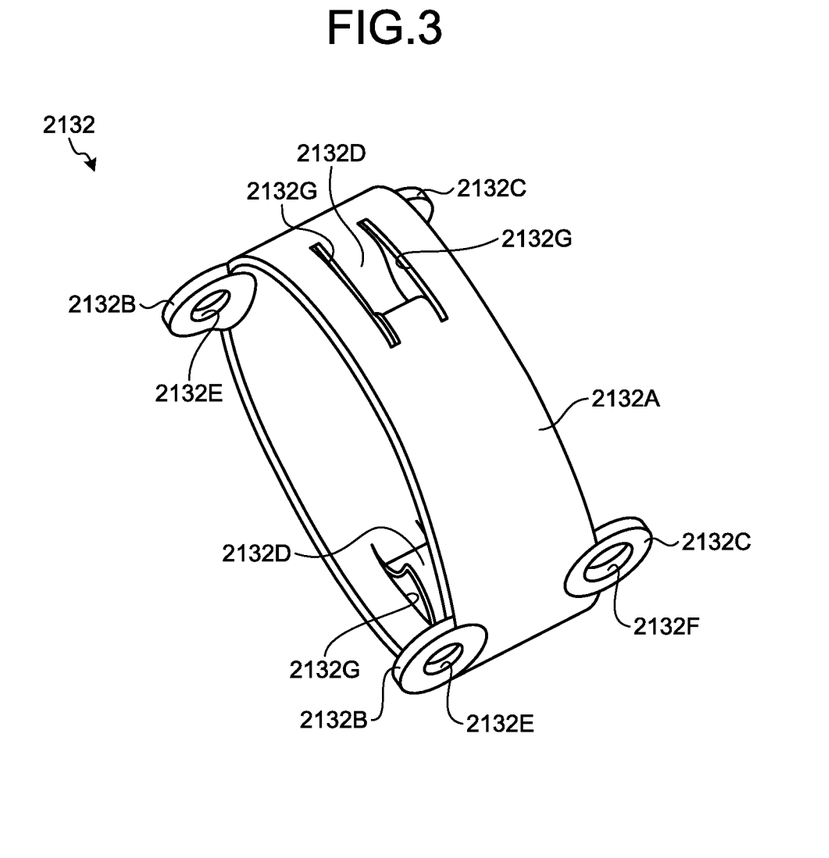
FIG. 3 is a perspective view showing a ring-shaped member illustrated in FIG. 2.

FIG. 3 is a perspective view showing the ring-shaped member 2132.

The plural ring-shaped members 2132 have a uniform shape. Therefore, only a shape of one of the ring-shaped members 2132 is explained in the following.

The ring-shaped member 2132 includes a cylindrical base 2132A, two pieces of first jut-out portions 2132B, two pieces of second jut-out portions 2132C, and two pieces of wire inserting portions 2132D as illustrated in FIG. 3.

The two pieces of first jut-out portions 2132B are portions arranged at rotationally-symmetrical positions by 180 degrees relative to a center axis of the base 2132A, jutting out toward a distal end side from an end of the base 2132A on the distal end side. In each of the two pieces of first jut-out members 2132B, a first pin-inserting hole 2132E piercing through to a front side and a rear side (piercing through in a direction perpendicular to the center axis of the base 2132A), through which a pin PN (FIG. 2) is inserted is formed.

The two pieces of second jut-out portions 2132C are portions jutting out toward a proximal end side from an end of the base 2132A on the proximal end side from respective positions opposing to the two pieces of first jut-out portions 2132B. In each of the two pieces of second jut-out members 2132C, a second pin-inserting hole 2132F piercing through to a front side and a rear side, through which the pin PN is inserted is formed similarly to the first jut-out portions 2132B.

Out of the plural ring-shaped members 2132, two ring-shaped members 2132 are joined to each other by superimposing the respective first jut-out members 2132B of one of the ring-shaped member 2132 with the respective second jut-out members 2132C of the other ring-shaped member 2132 and by inserting the pin PN in the first and second pin inserting holes 2132E, 2132F. That is, the ring-shaped members 2132 are joined to each other along an insertion direction into the body of the subject by a joining structure described above, and are rotatable about the pins PN (rotatable in a vertical direction in FIG. 2).

Moreover, out of the ring-shaped members 2132 joined to each other as described above, the ring-shaped member 2132 that is positioned at a proximal end is rotationally joined to the proximal end base 2131 at its distal end through the pin PN. The ring-shaped member 2132 positioned at the distal end is rotationally joined to the proximal end side of the distal end base 2133 through the pin PN.

The two pieces of wire inserting portions 2132D are portions through which two pieces of angle wires AW (corresponding to a wire according to the present disclosure (FIG. 2)) are inserted, respectively. The two pieces of wire inserting portions 2132D are arranged in the base 2132A at positions rotated from the respective first and second jut-out portions 2132B, 2132C by 90° with respect to the center axis of the base 2132A.

Specifically, in the base 2132A, at the positions rotated respectively from the first and second jut-out portions 2132B, 2132C by 90° with respect to the center axis of the base 2132A, a pair of slit holes 2132G (FIG. 3) extending along a peripheral direction of the base 2132A and opposing to each other along the center axis of the base 2132A are formed. The two pieces of wire inserting portions 2132D are parts corresponding to inner portions of the pair of respective slit holes 2132G bent toward the center axis of the base 2132A.

The two pieces of angle wires AW are put through the ring-shaped members 2132 so as to go through between the base 2132A and the wire inserting portion 2132D. The two pieces of angle wires AW are connected to the bending knob 221 at one end, and to the distal end base 2133 at the other end. That is, as the bending knob 221 is operated by a doctor or the like, the two pieces of angle wires AW are pulled or released appropriately, to bend the bendable tube 213A (bendable portion 213) in two directions, an upward direction and a downward direction, in FIG. 2.

Configuration of Flexible Board

Figure 4:
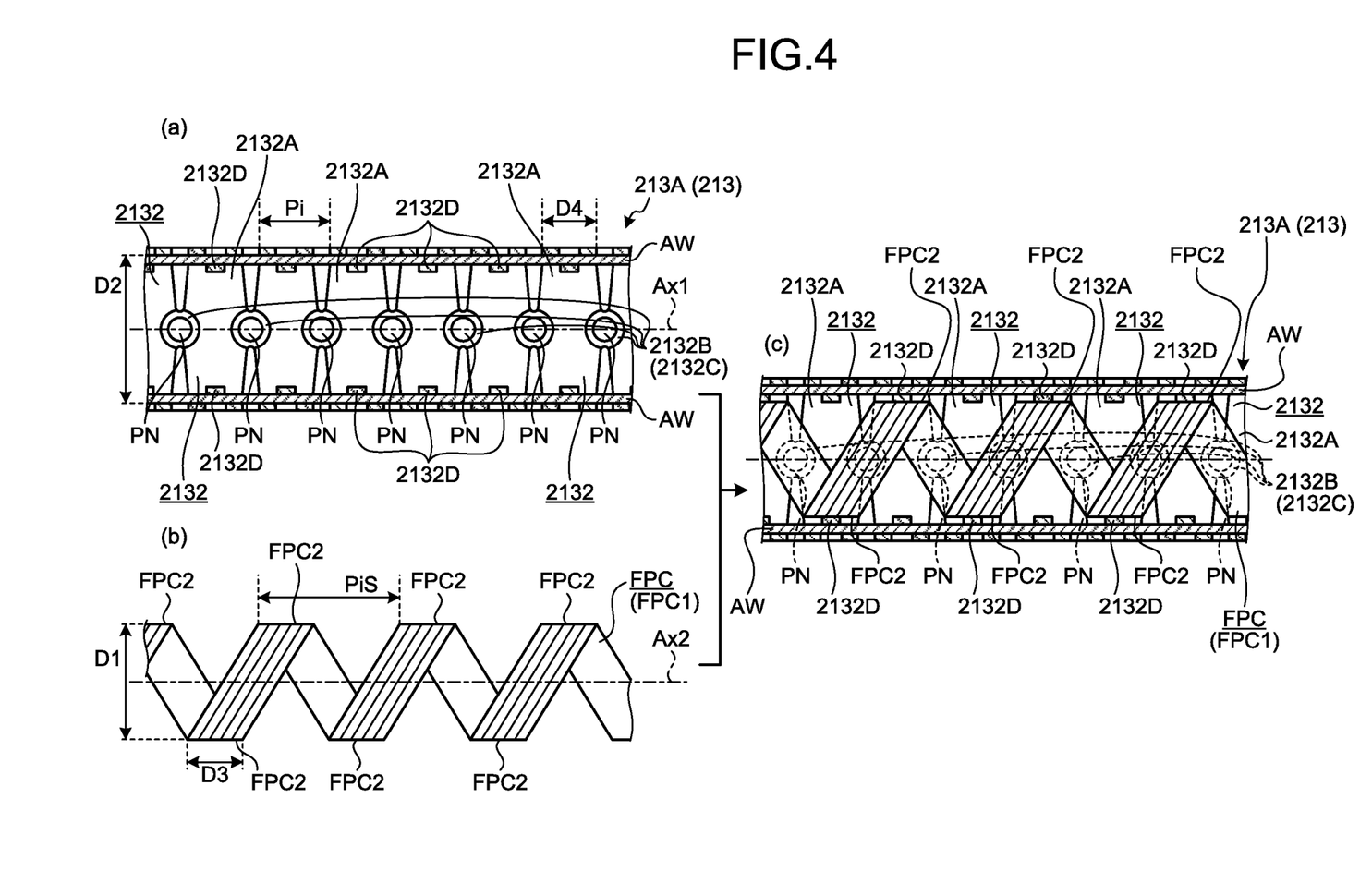
FIG. 4 shows arrangement of a flexible board that is arranged inside a bendable portion illustrated in FIG. 1 and FIG. 2.

FIG. 4 and FIG. 5 show arrangement of the flexible board FPC that is arranged inside the bendable portion 213. Specifically, a part (a) of FIG. 4 is a cross-section of the bendable tube 213A taken along a plane (plane including a center axis Ax1 of the bendable tube 213A) passing through the two pieces of wire inserting portions 2132D. A part (b) of FIG. 4 shows the flexible board FPC viewed from side. A part (c) of FIG. 4 is a cross-section corresponding to the part (a) of FIG. 4 and shows arrangement of the flexible board FPC inside the bendable tube 213A. In FIG. 4, illustration of the shield member 2134 and the covering member 2135 is omitted (only the bendable tube 213A is illustrated) similarly to FIG. 2 for convenience of explanation. FIG. 5 is a cross-section of the bendable portion 213 taken along a plane perpendicular to the center axis Ax1 of the bendable tube 213A. In FIG. 5, the flexible board FPC is indicated by chain double-dashed lines for convenience of explanation.

The flexible board FPC is an elongated sheet made from an insulating material, such as polyimide, on which a conductor pattern is formed, and is inserted through the bendable tube 213A. The flexible board FPC electrically connects the transducer unit 2111 and the signal cable CB that is routed to the distal end side of the flexible tube 214 through the conductor pattern.

Specifically, the flexible board FPC includes a helical portion FPC1 having a helical shape about a virtual line Ax2 (the part (b) of FIG. 4) that is parallel to the center axis Ax1 (the part (a) of FIG. 4) of the bendable tube 213A as illustrated in FIG. 4 or FIG. 5. In the flexible board FPC, an entire part except a part on a side of one end electrically connected to the transducer unit 2111 and a part on a side of the other end electrically connected to the signal cable CB is constituted of the helical portion FPC1.

In the present embodiment, an outer diameter dimension D1 (the part (b) of FIG. 4) of the helical portion FPC1 is set to be the same as an inner diameter dimension D2 (the part (a) of FIG. 4) of the bendable tube 213A (base 2132A). Moreover, a width dimension D3 (the part (b) of FIG. 4) of the flexible board FPC is set to the same as a length dimension D4 (the part (a) of FIG. 4) of the base 2132A in a direction parallel to the center axis Ax1 (insertion direction into the body of the subject). Furthermore, a helical pitch PiS (the part (b) of FIG. 4) of the helical portion FPC1 is set to be twice as long as a pitch Pi (the part (a) of FIG. 4) of the ring-shaped members 2132.

The flexible board FPC is arranged inside the bendable tube 213A as indicated below.

Specifically, the helical portion FPC1 is arranged along an inner surface of the bendable tube 213A. Moreover, respective portions FPC2 apart from each other with the helical pitch PiS in the helical portion FPC1 abut on an inner surface (one of the two pieces of wire inserting portions 2132D) of the respective ring-shaped members 2132 arranged periodically with a pitch twice as long as the pitch Pi out of the plural ring-shaped members 2132 as illustrated in the part (c) of FIG. 4 or FIG. 5. At this point, the respective portions FPC2 are positioned inside the respective ring-shaped members without protruding out of the ring-shaped members as illustrated in the part (c) of FIG. 4. All of the respective portions FPC2 abut on the respective wire inserting portions 2132D are fixed to the respective wire inserting portions 2132D with adhesive, solder, or the like.

The ultrasound endoscope 2 according to the present embodiment explained above has the helical portion FPC1 formed in a helical shape along the inner surface of the bendable tube 213A. Therefore, it is possible to make the flexible board FPC (helical portion FPC1) follow bending movement of the bendable tube 213A (bendable portion 213) according to an operation input to the operating unit 22, and to prevent the flexible board FPC from being snapped. Moreover, a part of the helical portion FPC1 is fixed to the inner surface of the bendable tube 213A. Therefore, even when the operating unit 22 is operated, the flexible board FPC is not pulled toward the proximal ends side, and the flexible board FPC (helical portion FPC1) does not act to squeeze contents (the light guide LG, the image guide IG, the tube TB, the treatment tool tube CH), and the like).

Therefore, according to the ultrasound endoscope 2 according to the present embodiment, an effect that a break of the flexible board FPC can be prevented is obtained. Moreover, because the flexible board FPC does not act to squeeze contents, the contents are not damaged.

Particularly, because the bendable tube 213A makes bending movements, the flexible board FPC (helical portion FPC1) arranged inside the bendable tube 213A are also likely to move (likely to make wild movements) with respect to the bendable tube 213A. Therefore, by fixing a part of the helical portion FPC1 to the inner surface of the bendable tube 213A, that makes large movement, to the bendable tube 214 that makes small movement, it is possible to make the helical portion FPC1 to follow the bending movements of the bendable tube 213A and to suppress movement (wild movement) of the helical portion FPC1 with respect to the bendable tube 213A. By suppressing movements of the helical portion FPC1 with respect to the bendable tube 213A, a break of the flexible board FPC and a damage of contents can be effectively prevented.

Furthermore, in the ultrasound endoscope 2 according to the present embodiment, the respective portions FPC2 apart from each other with the helical pitch PiS in the helical portion FPC1 abut on the inner surface (wire inserting portions 2132D) of the respective ring-shaped members 2132 that are arranged periodically with a pitch twice as long as the pitch Pi out of the plural ring-shaped members 2132. All of the respective portions FPC2 abutting on the respective wire inserting portions 2132D are fixed to the wire inserting portions 2132D by adhesive, solder, or the like. Therefore, the bendable tube 213A and the helical portion FPC1 are unified with the each other, and it is possible to make sure that the helical portion FPC1 follows the bending movements of the bendable tube 213A. That is, by preventing movement of the helical portion FPC1 with respect to the bendable tube 213A, a break of the flexible board FPC and a damage of contents can be effectively prevented, and to reduce an amount of bending force of the bendable tube 213A to improve the operability.

Particularly, the wire inserting portion 2132D is a part at which largest movement are made in the ring-shaped member 2132 at the time of bending movements of the bendable tube 213A. Therefore, it is possible to make sure that the helical portion FPC1 follows the bending movement of the bendable tube 213A by fixing the helical portion FPC1 to the wire inserting portion 2132D making large movements.

Moreover, the width dimension D3 of the flexible board FPC is set to the same dimension as the length dimension D4 in a direction parallel to the center axis Ax1 of the base 2132A. Furthermore, the respective portions FPC2 are positioned inside the respective ring-shaped members 2132 without protruding out of the ring-shaped members 2132. Therefore, mechanical interference between the portions FPC2 and the respective adjacent ring-shaped members 2132 at the time of bending movements of the bendable tube 213A does not occur. Accordingly, an amount of bending force of the bendable tube 213A can be further reduced compared to a case in which the respective portions FPC2 protrude out of the ring-shaped members 2132, and the operability can be improved.

Other Embodiments

The embodiment has been explained, but the present disclosure is not to be limited only to the embodiment described above.

Although all the respective portions FPC2 abutting on the wire-inserting portions 2132D are fixed to the corresponding wire-inserting portions 2132D in the helical portion FPC1 by adhesive, solder, or the like in the embodiment described above, it is not limited thereto. As long as a part of the helical portion FPC1 is fixed to the inner surface of the bendable tube 213A, the fixing position is not limited.

Moreover, the fixing of the helical portion FPC1 and the bendable tube 213A is not limited to be done by adhesive or solder, but by providing an engaging structure with which the helical portion FPC1 and the bendable tube 213A engage with each other, a fixing structure using the engaging structure can be applied.

Although the respective portions FPC2 apart from each other with the helical pitch PiS in the helical portion FPC1 abut on the inner surface of the respective ring-shaped members 2132 that are arranged periodically with a pitch twice as long as the pitch Pi (PiS=2×Pi) out of the plural ring-shaped members 2132 in the embodiment described above, it is not limited thereto. As long as the respective portions FPC2 apart from each other with the helical pitch PiS in the helical portion FPC1 abut on the inner surface of the respective ring-shaped members 2132 arranged periodically with a pitch 2n times (n is a positive integer) as long as the pitch Pi (PiS=2n), other helical pitches can be applied.

Although the bendable tube 213A is configured to be bendable in two directions (the upward direction and the downward direction in FIG. 2) in the embodiment described above, it is not limited thereto. It can be configured to be bendable in more than two directions, for example, four directions (the upward direction, the downward direction, a leftward direction, and a rightward direction in FIG. 2).

Although the endoscope system 1 has both the function of generating ultrasound images and the function of generating endoscopic images in the embodiment described above, it is not limited thereto. It can be configured to have only the function of generating ultrasound images.

In the embodiment described above, the endoscope system 1 can be used in an industrial field, not limited to the medical field, and can be used as an endoscope system to observe the inside of a subject, such as a mechanical structure, or the like.

In an ultrasound endoscope according to the present disclosure, a flexible board has a helical portion that is formed in a helical shape following an inner surface of a bendable tube. Therefore, the flexible board (the helical portion) is made to follow a bending movement of the bendable tube in accordance with an operation input to an operating unit, thereby preventing the flexible board from being bent. Moreover, the helical portion is fixed to an inner surface of the bendable tube at a part. Therefore, even when an operation is input to the operating unit, the flexible board is not pulled toward a proximal end side, and the flexible board (the helical portion) does not act to squeeze a content.

Therefore, according to the ultrasound endoscope according to the present disclosure, it is possible to prevent a break of the flexible board, and a damage of the content.

Additional advantages and modifications will readily occur to those skilled in the art. Therefore, the disclosure in its broader aspects is not limited to the specific details and representative embodiments described herein. Accordingly, various modifications may be made without departing from the spirit or scope of the general inventive concept as defined by the appended claims and their equivalents.

What is claimed is:

1. An ultrasound endoscope comprising:
    an insertion portion extending along a longitudinal axis direction, the insertion portion comprising a bendable tube and a flexible tube; and
    a transducer unit arranged on a distal end side of the insertion portion, the transducer unit being configured to transmit and receive an ultrasonic wave;
    the bendable tube being arranged proximally relative to the transducer unit, the bendable tube including a plurality of ring-shaped members that are rotatably joined with each other along the longitudinal axis direction such that the bendable tube is bendable in at least first and second directions;
    the flexible tube being arranged proximally relative to the bendable tube; and
    wherein a flexible board disposed on an inside of the bendable tube, the flexible board being configured to electrically connect to the transducer unit, and
    the flexible board includes a helical portion formed in a helical shape within an inner surface of each of the plurality of ring-shaped members, the helical portion being fixed to the inner surface at a fixing portion of the inner surface at at least every other ring-shaped member of the plurality of ring-shaped members.

2. The ultrasound endoscope according to claim 1, wherein a helical pitch of the helical portion is at least twice a pitch of the plurality of ring-shaped members, the pitch of the plurality of ring-shaped members being a length in the longitudinal axis direction from a point on one of the plurality of ring-shaped members to a corresponding point on an adjacent ring-shaped member of the plurality of ring-shaped members.

3. The ultrasound endoscope according to claim 2, wherein the helical portion is fixed at the fixing portion at every other ring-shaped member of the plurality of ring-shaped members and the helical pitch of the helical portion is twice the pitch of the plurality of ring-shaped members.

4. The ultrasound endoscope according to claim 1, wherein a width dimension of the flexible board in the helical portion is set to be equal to or smaller than a length dimension of each of the plurality of ring-shaped members in the longitudinal axis direction.

5. The ultrasound endoscope according to claim 1, further comprising:
    first and second wires configured to bend the plurality of ring-shaped members in the at least first and second directions, respectively,
    wherein each of the ring-shaped members includes first and second wire insertion portions through which the first and second wires are respectively inserted, the inner surface of each of the plurality of ring-shaped members includes a wire insertion inner surface of each of the first and second wire insertion portions that protrudes radially inward from other portions of the inner surface of each of the plurality of ring-shaped members, and
    the fixing portion of the inner surface comprises the wire insertion inner surface.

6. An insertion portion for an ultrasound endoscope, the insertion portion comprising:
    a transducer unit being configured to transmit and receive an ultrasonic wave;
    a bendable tube arranged proximally relative to the transducer unit, the bendable tube including a plurality of ring-shaped members that are rotatably joined with each other along a longitudinal axis direction such that the bendable tube is bendable in at least first and second directions;
    a flexible tube arranged proximally relative to the bendable tube; and
    a flexible board disposed on an inside of the bendable tube, the flexible board being configured to electrically connect to the transducer unit,
    wherein the flexible board includes a helical portion formed in a helical shape within an inner surface of each of the plurality of ring-shaped members, the helical portion being fixed to the inner surface at a fixing portion of the inner surface at at least every other ring-shaped member of the plurality of ring-shaped members.

7. The insertion portion according to claim 6, wherein a helical pitch of the helical portion is at least twice a pitch of the plurality of ring-shaped members, the pitch of the plurality of ring-shaped members being a length in the longitudinal axis direction from a point on one of the plurality of ring-shaped members to a corresponding point on an adjacent ring-shaped member of the plurality of ring-shaped members.

8. The insertion portion according to claim 7, wherein the helical portion is fixed at the fixing portion at every other ring-shaped member of the plurality of ring-shaped members and the helical pitch of the helical portion is twice the pitch of the plurality of ring-shaped members.

9. The insertion portion according to claim 1, wherein a width dimension of the flexible board in the helical portion is set to be equal to or smaller than a length dimension of each of the plurality of ring-shaped members in the longitudinal axis direction.

10. The insertion portion according to claim 6, further comprising:
    first and second wires configured to bend the plurality of ring-shaped members in the at least first and second directions, respectively,
    wherein each of the ring-shaped members includes first and second wire insertion portions through which the first and second wires are respectively inserted, the inner surface of each of the plurality of ring-shaped members includes a wire insertion inner surface of each of the first and second wire insertion portions that protrudes radially inward from other portions of the inner surface of each of the plurality of ring-shaped members, and the fixing portion of the inner surface comprises the wire insertion inner surface.

11. An ultrasound endoscope comprising:

an insertion portion extending along a longitudinal axis direction, the insertion portion comprising a bendable tube and a flexible tube; and a transducer unit arranged on a distal end side of the insertion portion, the transducer unit being configured to transmit and receive an ultrasonic wave;

the bendable tube being arranged proximally relative to the transducer unit, the bendable tube including a plurality of ring-shaped members that are rotatably joined with each other along the longitudinal axis direction such that the bendable tube is bendable in at least first and second directions;

the flexible tube being arranged proximally relative to the bendable tube;

wherein a flexible board disposed on an inside of the bendable tube, the flexible board being configured to electrically connect to the transducer unit, the flexible substrate having a first end, a second end and a middle portion between the first and second end; and the middle portion of the flexible board includes a helical portion formed in a helical shape within an inner surface of each of the plurality of ring-shaped members, the middle portion of the helical portion being fixed to the inner surface at a fixing portion of the inner surface at at least two of the plurality of ring-shaped members.

12. The ultrasound endoscope according to claim 11, wherein the middle portion of the helical portion is fixed to the inner surface at the fixing portion of the inner surface at at least every other ring-shaped member of the plurality of ring-shaped members.

13. The ultrasound endoscope according to claim 12, wherein a helical pitch of the helical portion is at least twice a pitch of the plurality of ring-shaped members, the pitch of the plurality of ring-shaped members being a length in the longitudinal axis direction from a point on one of the plurality of ring-shaped members to a corresponding point on an adjacent ring-shaped member of the plurality of ring-shaped members.

14. The ultrasound endoscope according to claim 13, wherein the helical portion is fixed at the fixing portion at every other ring-shaped member of the plurality of ring-shaped members and the helical pitch of the helical portion is twice the pitch of the plurality of ring-shaped members.

15. The ultrasound endoscope according to claim 11, wherein a width dimension of the flexible board in the helical portion is set to be equal to or smaller than a length dimension of each of the plurality of ring-shaped members in the longitudinal axis direction.

16. The ultrasound endoscope according to claim 11, further comprising:

first and second wires configured to bend the plurality of ring-shaped members in the at least first and second directions, respectively, wherein each of the ring-shaped members includes first and second wire insertion portions through which the first and second wires are respectively inserted, the inner surface of each of the plurality of ring-shaped members includes a wire insertion inner surface of each of the first and second wire insertion portions that protrudes radially inward from other portions of the inner surface of each of the plurality of ring-shaped members, and the fixing portion of the inner surface comprises the wire insertion inner surface.

* * * * *